(12) United States Patent
Clements et al.

(10) Patent No.: US 11,602,359 B2
(45) Date of Patent: Mar. 14, 2023

(54) RASP HANDLE ADAPTER

(71) Applicant: Zimmer, Inc., Warsaw, IN (US)

(72) Inventors: Joshua Clements, Fort Wayne, IN (US); James S. Collins, Fort Wayne, IN (US); Christopher A Gray, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 238 days.

(21) Appl. No.: 17/149,514

(22) Filed: Jan. 14, 2021

(65) Prior Publication Data

US 2021/0228219 A1 Jul. 29, 2021

Related U.S. Application Data

(60) Provisional application No. 62/965,543, filed on Jan. 24, 2020.

(51) Int. Cl.
*A61B 17/16* (2006.01)
*A61B 17/00* (2006.01)

(52) U.S. Cl.
CPC .......... *A61B 17/1659* (2013.01); *A61B 2017/00486* (2013.01)

(58) Field of Classification Search
CPC ... A61B 17/16; A61B 17/1613; A61B 17/162; A61B 17/1659; A61B 17/1662; A61B 17/1664; A61B 17/1668; A61B 2017/00486

See application file for complete search history.

(56) References Cited

U.S. PATENT DOCUMENTS

| | | | |
|---|---|---|---|
| 4,306,550 A | * | 12/1981 | Forte .......................... A61F 2/36 606/85 |
| 4,583,270 A | | 4/1986 | Kenna |
| 4,587,964 A | | 5/1986 | Walker et al. |
| 4,601,289 A | | 7/1986 | Chlarizzio et al. |

(Continued)

FOREIGN PATENT DOCUMENTS

| CN | 113768580 A | * 12/2021 |
|---|---|---|
| EP | 0496629 A1 | 7/1992 |

(Continued)

OTHER PUBLICATIONS

"U.S. Appl. No. 14/062,286, Final Office Action dated Oct. 31, 2019", 12 pgs.

(Continued)

*Primary Examiner* — Eric S Gibson
(74) *Attorney, Agent, or Firm* — Schwegman Lundberg & Woessner, P.A.

(57) ABSTRACT

Disclosed herein are rasp adapters, rasp systems, and method of use thereof. The rasp adapter can include a body and a retention element. The body can define a body cavity, a handle opening, and a trunnion bore. The retention element can be located within the body cavity and can include a knuckle and a heal. The knuckle can be located proximate to and movable into and out of the trunnion bore. The heal can be located proximate the handle opening. Movement of the retention element due to a force applied to the heal can cause movement of the retention element and movement of the knuckle into the trunnion bore.

20 Claims, 12 Drawing Sheets

(56) References Cited

U.S. PATENT DOCUMENTS

| | | | |
|---|---|---|---|
| 4,765,328 A * | 8/1988 | Keller | A61B 17/1659 |
| | | | 606/85 |
| 4,921,493 A * | 5/1990 | Webb, Jr. | A61B 17/1659 |
| | | | 606/85 |
| 4,922,574 A | 5/1990 | Heiligenthal et al. | |
| 4,990,149 A * | 2/1991 | Fallin | A61B 17/1659 |
| | | | 606/85 |
| 5,089,003 A * | 2/1992 | Fallin | A61B 17/1668 |
| | | | 606/85 |
| 5,089,033 A | 2/1992 | Wijmans | |
| 5,190,549 A | 3/1993 | Miller et al. | |
| 5,190,550 A | 3/1993 | Miller et al. | |
| 5,261,915 A | 11/1993 | Duriacher et al. | |
| 5,324,293 A | 6/1994 | Rehmann | |
| 5,350,381 A | 9/1994 | Melton | |
| 5,352,230 A * | 10/1994 | Hood | B25D 9/08 |
| | | | 606/86 R |
| 5,531,750 A | 7/1996 | Even-Esh | |
| 5,634,735 A | 6/1997 | Horton et al. | |
| 5,643,271 A | 7/1997 | Sederholm et al. | |
| 5,720,750 A | 2/1998 | Koller et al. | |
| 5,769,853 A | 6/1998 | Quetlin | |
| 5,810,830 A | 9/1998 | Noble et al. | |
| 5,820,009 A | 10/1998 | Melling et al. | |
| 5,827,290 A | 10/1998 | Bradley | |
| 5,993,455 A | 11/1999 | Noble | |
| 6,190,416 B1 | 2/2001 | Choteau et al. | |
| 6,205,884 B1 | 3/2001 | Foley et al. | |
| 6,224,605 B1 * | 5/2001 | Anderson | A61B 17/175 |
| | | | 606/85 |
| 6,238,435 B1 | 5/2001 | Meulink et al. | |
| 6,368,324 B1 | 4/2002 | Dinger | |
| 6,527,803 B1 | 3/2003 | Crozet et al. | |
| 6,537,280 B2 | 3/2003 | Dinger et al. | |
| 6,610,066 B2 | 8/2003 | Dinger et al. | |
| 6,663,636 B1 | 12/2003 | Lin | |
| 6,977,000 B2 * | 12/2005 | Vanasse | A61F 2/4684 |
| | | | 623/22.45 |
| 7,010,996 B2 | 3/2006 | Schick et al. | |
| 7,014,156 B2 | 3/2006 | Apezetxea et al. | |
| 7,124,479 B2 | 10/2006 | Johnson | |
| 7,322,843 B1 | 1/2008 | Lee et al. | |
| 7,325,693 B2 | 2/2008 | Bruns et al. | |
| 7,396,054 B2 | 7/2008 | Carrier | |
| 7,591,821 B2 | 9/2009 | Kiernan | |
| 7,749,227 B2 | 7/2010 | Lechot et al. | |
| 7,922,726 B2 | 4/2011 | White | |
| 7,935,125 B2 | 5/2011 | Bastian et al. | |
| 7,938,679 B2 | 5/2011 | Wadsworth et al. | |
| 7,976,548 B2 | 7/2011 | Burgi et al. | |
| 8,021,365 B2 | 9/2011 | Phan | |
| 8,216,240 B2 | 7/2012 | Dewey | |
| 8,337,502 B2 | 12/2012 | Bastian et al. | |
| 8,449,619 B2 * | 5/2013 | Metcalfe | A61F 2/4684 |
| | | | 623/22.11 |
| 8,657,824 B2 * | 2/2014 | Sharp | A61B 17/1604 |
| | | | 606/80 |
| 9,526,512 B2 * | 12/2016 | Sharp | A61B 17/1668 |
| 10,667,798 B2 | 6/2020 | Thomsen et al. | |
| 2005/0234462 A1 | 10/2005 | Hershberger | |
| 2005/0234463 A1 | 10/2005 | Hershberger et al. | |
| 2006/0015188 A1 * | 1/2006 | Grimes | A61F 2/3601 |
| | | | 623/23.22 |
| 2006/0122701 A1 | 6/2006 | Kiester | |
| 2006/0162707 A1 | 7/2006 | Peek et al. | |
| 2006/0241625 A1 * | 10/2006 | Metcalfe | A61B 17/162 |
| | | | 606/79 |
| 2007/0167952 A1 * | 7/2007 | Burgi | A61B 17/1666 |
| | | | 606/99 |
| 2007/0233134 A1 * | 10/2007 | Bastian | A61F 2/4607 |
| | | | 606/85 |
| 2008/0004628 A1 | 1/2008 | White | |
| 2008/0033444 A1 * | 2/2008 | Bastian | A61B 17/1668 |
| | | | 606/85 |
| 2008/0077241 A1 | 3/2008 | Nguyen | |
| 2008/0172061 A1 | 7/2008 | Ragbir | |
| 2008/0177265 A1 | 7/2008 | Lechot | |
| 2008/0195101 A1 | 8/2008 | Lechot et al. | |
| 2008/0255565 A1 * | 10/2008 | Fletcher | A61B 17/1668 |
| | | | 606/80 |
| 2009/0218828 A1 | 9/2009 | Schumacher | |
| 2010/0023016 A1 | 1/2010 | Botimer | |
| 2010/0121331 A1 * | 5/2010 | Sharp | A61F 2/4607 |
| | | | 606/80 |
| 2011/0160734 A1 | 6/2011 | Bastian et al. | |
| 2011/0160733 A1 | 7/2011 | Wallstein et al. | |
| 2012/0083769 A1 | 4/2012 | Burgi et al. | |
| 2014/0121650 A1 | 5/2014 | Thomsen et al. | |
| 2014/0163561 A1 * | 6/2014 | Sharp | A61F 2/4607 |
| | | | 606/99 |
| 2017/0100134 A1 * | 4/2017 | Sharp | A61F 2/4607 |
| 2021/0228219 A1 * | 7/2021 | Clements | A61B 17/162 |
| 2021/0361296 A1 * | 11/2021 | Zimmerman | A61B 17/1659 |
| 2022/0313336 A1 * | 10/2022 | Zapari | A61F 2/4603 |

FOREIGN PATENT DOCUMENTS

| | | | | |
|---|---|---|---|---|
| EP | 1854416 A1 | | 10/1994 | |
| EP | 1011902 B1 | | 12/2001 | |
| EP | 2501315 B1 | * | 10/2017 | A61B 17/1604 |
| EP | 3338722 A2 | * | 6/2018 | A61B 17/1604 |
| ES | 2659822 T3 | * | 3/2018 | A61B 17/1604 |
| JP | 2015091420 A | * | 5/2015 | A61B 17/1604 |
| JP | 5968785 B2 | * | 8/2016 | A61B 17/1604 |
| JP | 6025182 B2 | * | 11/2016 | A61B 17/1604 |
| JP | 2017029771 A | * | 2/2017 | A61B 17/1604 |
| JP | 2018086520 A | * | 6/2018 | A61B 17/1604 |
| JP | 2019171164 A | * | 10/2019 | A61B 17/1604 |
| WO | WO-2006019877 A1 | * | 2/2006 | A61B 17/1668 |
| WO | WO-2011063173 A2 | * | 5/2011 | A61B 17/1604 |

OTHER PUBLICATIONS

"U.S. Appl. No. 14/062,286, Final Office Action dated Nov. 26, 2018", 20 pgs.

"U.S. Appl. No. 14/062,286, Non Final Office Action dated Jan. 27, 2017", 18 pgs.

"U.S. Appl. No. 14/062,286, Non Final Office Action dated Mar. 21, 2019", 20 pgs.

"U.S. Appl. No. 14/062,286, Non Final Office Action dated Apr. 3, 2018", 19 pgs.

"U.S. Appl. No. 14/062,286, Non Final Office Action dated Jun. 27, 2016", 14 pgs.

"U.S. Appl. No. 14/062,286, Non Final Office Action dated Aug. 4, 2017", 11 pgs.

"U.S. Appl. No. 14/062,286, Notice of Allowance dated Feb. 3, 2020", 9 pgs.

"U.S. Appl. No. 14/062,286, Preliminary Amendment filed Dec. 10, 2013", 9 pgs.

"U.S. Appl. No. 14/062,286, Response field Jun. 21, 2019 to Non-Final Office Action dated Mar. 21, 2019", 18 pgs.

"U.S. Appl. No. 14/062,286, Response filed Feb. 26, 2019 to Final Office Action dated Nov. 26, 2018", 10 pgs.

"U.S. Appl. No. 14/062,286, Response filed Mar. 14, 2016 to Restriction Requirement dated Jan. 14, 2016", 7 pgs.

"U.S. Appl. No. 14/062,286, Response filed Apr. 27, 2017 to Non-Final Office Action dated Jan. 27, 2017", 15 pgs.

"U.S. Appl. No. 14/062,286, Response filed Jul. 2, 2018 to Non Final Office Action dated Apr. 3, 2018", 8 pgs.

"U.S. Appl. No. 14/062,286, Response filed Sep. 23, 2016 to Non Final Office Action dated Jun. 27, 16", 11 pgs.

"U.S. Appl. No. 14/062,286, Response filed Nov. 6, 2017 to Non Final Office Action dated Aug. 4, 2017", 14 pgs.

"U.S. Appl. No. 14/062,286, Response filed Dec. 30, 2019 to Final Office Action dated Oct. 31, 2019", 9 pgs.

"U.S. Appl. No. 14/062,286, Restriction Requirement datead Jan. 14, 2016", 7 pgs.

(56) References Cited

OTHER PUBLICATIONS

U.S. Appl. No. 14/062,286, now U.S. Pat. No. 10,667,798, filed Oct. 24, 2013, Surgical Tool Handle Assemblies and Related Methods.

* cited by examiner

RASP HANDLE ADAPTER

PRIORITY CLAIM

The present application claims the benefit of priority to U.S. Provisional Application No. 62/965,543, filed Jan. 24, 2020, the contents of which is hereby incorporated by reference in its entirety.

FIELD OF THE DISCLOSURE

The present disclosure relates to adapters. Specifically, the present disclosure relates to rasp handle adapters and methods of use thereof.

BACKGROUND

During various surgical procedures, a rasp can be used to prepare a bone to receive an implant. For example, during a hip arthroplasty procedure a stem can be implanted into a femur. However, before the stem can be implanted, a rasp can be used to prepare the femoral canal. The rasp can be removably connected to a rasp handle. By having the rasp be removably connected to the rasp handle, different rasps each having a different size and/or roughness can be connected to the rasp handle.

SUMMARY

The following, non-limiting examples, detail certain aspects of the present subject matter to solve the challenges and provide the benefits discussed herein, among others.

Example 1 is a rasp adapter comprising: a body that defines a body cavity, a handle opening, and a trunnion bore; and a retention element located within the body cavity, the retention element including: a knuckle located proximate to and movable into and out of the trunnion bore, and a heal located proximate the handle opening, wherein movement of the retention element due to a force applied to the heal causes movement of the retention element and movement of the knuckle into the trunnion bore.

In Example 2, the subject matter of Example 1 optionally includes wherein the retention element is coupled to the body via a spring.

In Example 3, the subject matter of any one or more of Examples 1-2 optionally include a trunnion protruding from a superior surface of the body, the trunnion defining at least one trunnion notch.

In Example 4, the subject matter of Example 3 optionally includes wherein the trunnion, the retention element, and the body are a monolithic component.

In Example 5, the subject matter of any one or more of Examples 1-4 optionally include a protrusion extending from an inferior surface of the body.

In Example 6, the subject matter of any one or more of Examples 1-5 optionally include a stop located proximate the knuckle.

In Example 7, the subject matter of any one or more of Examples 1-6 optionally include wherein a surface of the body cavity defines an arch structure with an apex proximate the knuckle.

In Example 8, the subject matter of any one or more of Examples 1-7 optionally include wherein the knuckle defines a lead in proximate the trunnion bore.

In Example 9, the subject matter of any one or more of Examples 1-8 optionally include a pin pivotably coupling the retention element to the body.

In Example 10, the subject matter of any one or more of Examples 1-9 optionally include a biasing element located within the body cavity and arranged to bias the knuckle into the trunnion bore.

Example 11 is a rasp adapter comprising: a body having an interior surface that defines a body cavity, a handle opening, and a trunnion bore; a trunnion protruding from a superior surface of the body; a biasing element located within the body cavity; and a retention element located within the body cavity and coupled to the body via the biasing element, the retention element including: a knuckle located proximate to and moveable into and out of the trunnion bore, and a heal located proximate the handle opening, wherein movement of the retention element due to a force applied to the heal causes movement of the retention element and movement of the knuckle into the trunnion bore.

In Example 12, the subject matter of Example 11 optionally includes wherein the biasing element comprises a plurality of spring legs.

In Example 13, the subject matter of any one or more of Examples 11-12 optionally include wherein the trunnion defines at least one trunnion notch.

In Example 14, the subject matter of any one or more of Examples 11-13 optionally include a protrusion extending from an inferior surface of the body.

In Example 15, the subject matter of any one or more of Examples 11-14 optionally include wherein the interior surface of the body cavity defines an arch structure with an apex proximate the knuckle.

In Example 16, the subject matter of any one or more of Examples 11-15 optionally include wherein the knuckle defines a lead in proximate the trunnion bore.

In Example 17, the subject matter of any one or more of Examples 11-16 optionally include wherein the biasing element, the retention element, and the body are a monolithic component.

Example 18 is a rasp system comprising: a handle having a first end that defines a first trunnion bore and a handle pin; and a plurality of adapters, each of the plurality of adapters comprising: a body having an interior surface that defines a body cavity, a handle opening sized to receive the handle pin, and a second trunnion bore; a trunnion protruding from a superior surface of the body, the trunnion defining at least one trunnion notch; a biasing element located within the body cavity; and a retention element located within the body cavity and coupled to the body via the biasing element, the retention element including a knuckle located proximate to and moveable into and out of the second trunnion bore, and a heal located proximate the handle opening, wherein the biasing element of at least one of the plurality of adapters comprises a plurality of spring legs, wherein the knuckle of at least one of the plurality of adapters defines a lead in proximate the second trunnion bore, wherein upon insertion of the handle pin into the handle opening and the trunnion into the first trunnion bore, the handle pin contacts the heal and causes the knuckle to move into the second trunnion bore, wherein a combination of trunnion and second trunnion bore sizes differs for each of the plurality of adapters.

In Example 19, the subject matter of Example 18 optionally includes wherein at least one of the plurality of adapters comprises a protrusion extending from an inferior surface of the body.

In Example 20, the subject matter of any one or more of Examples 18-19 optionally include wherein the interior surface of at least one of the plurality of adapters defines an arch structure with an apex proximate the knuckle.

In Example 21, the rasp adaptor or rasp systems of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
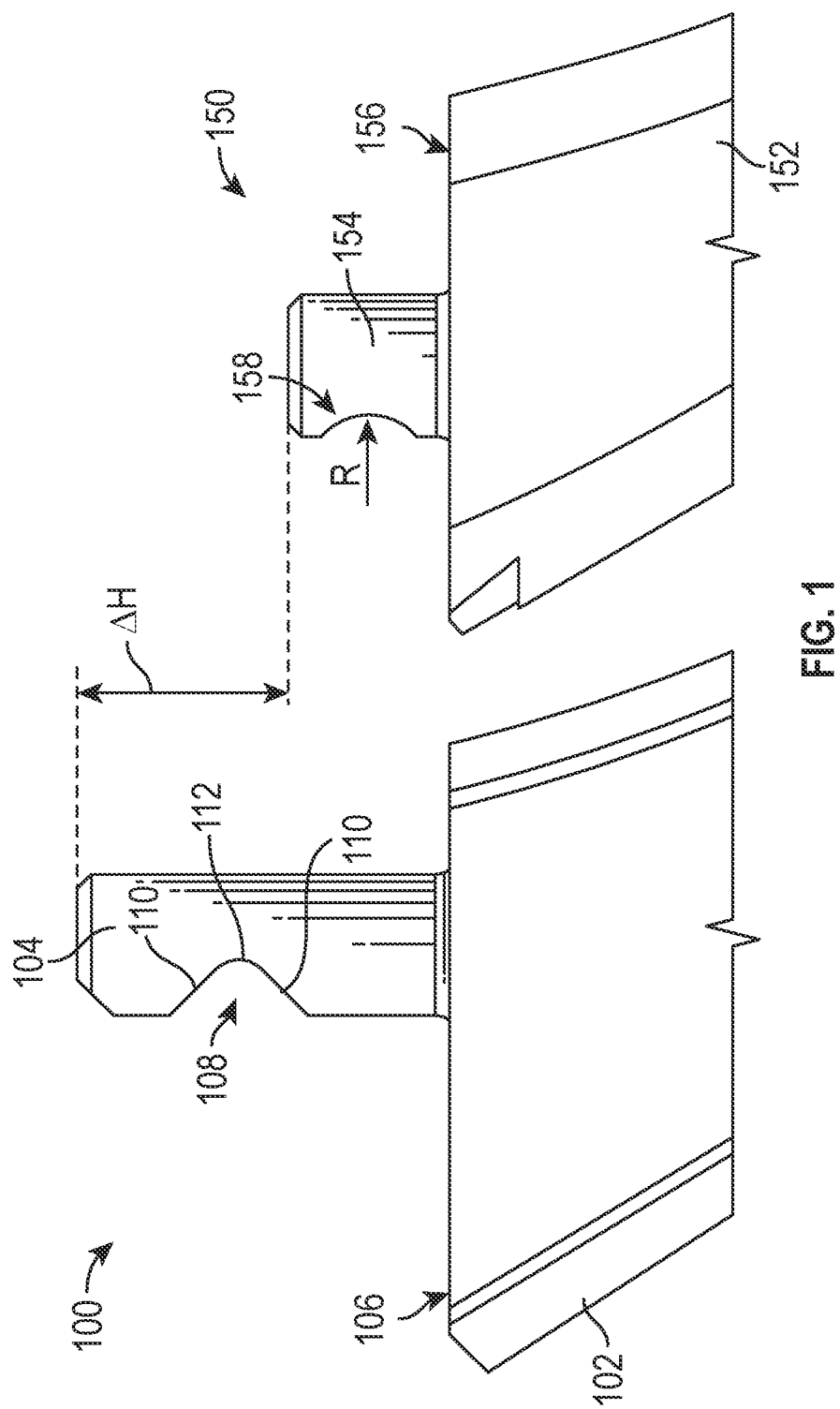
FIG. 1 shows rasp geometries in accordance with at least one example of the present disclosure.

Rasps, also referred to as broaches, made by different manufactures and/or different generations of rasps from the same manufacturer can have different connection geometries. The different connection geometries can make it difficult and/or impossible to utilize a single rasp handle with the differing rasps. The different connection geometries also can make it difficult and/or impossible to utilize different rasp handles for an individual rasp. For example, a surgeon may prefer to use a particular rasp that has a connection geometry for a first rasp handle, but due to size constraints or familiarity with a particular rasp handle the surgeon may not be able to use the particular rasp handle and may have to use a second rasp handle.

As disclosed herein, a rasp adapter can allow the use of rasps and rasp handles that have different connection geometries. As a result, surgeons that have developed a preference for a particular rasp handle based on their approach and experience, can use different rasps or vice versa. Without the rasp adapters disclosed herein, new rasp handles and/or rasps have to be designed and manufactured mimicking the preferred handle design with a modified connection linkage. Furthermore, surgeons typically require multiple rasp handles to accommodate multiple surgeries occurring in a single day and the asymmetric nature of some handles (i.e. handle designed to access left and right sides of the patient's body). Design and regulatory approval of new rasp handles and rasps can consume a lot of human and financial capital and take upwards of 12 months or longer. Production of each new handle can cost several thousands of dollars as well.

The adapters disclosed herein allow for a simplified component that can be manufactured at a reduced cost and delivery time to allow a single handle to be used with rasps having different connection geometries than the handle. Further, the adapters disclosed herein can allow surgeons to select any of the already existing rasps handles that are available from different manufacturers or generations of rasp handles.

The adapters disclosed herein can include a male post geometry, sometimes referred to as a trunnion, on a superior face that mimics the rasp post designed to mate with the preferred handle. The inferior surface of the adapters can have a complementary female geometry designed to connect to the male rasp post of the preferred rasp and/or stem system. Additionally, the inferior surface can incorporate an anti-rotation feature, such as a tab, peg, or other protrusion that can mimic that of the rasp handle designed to mate with the preferred rasp and/or stem system.

The adapters disclosed herein also can have an integral biasing member, such as a spring feature, that allows for easy assembly and disassembly onto the rasps using only manual forces instead of special fixtures and/or tooling. The biasing element can be designed to stiffen and lock once the rasp handle engages the adapter to prevent the assembly from separating while under working loads during bone preparation (e.g., impaction and retraction).

As disclosed herein, multiple adapters can be used during a single surgery such that multiple rasps sizes can be assembled to expedite to the rasping process. The rasp handle can then be assembled to each rasp/adapter assembly and the bone prepared. Once the final rasp/adapter assembly has been utilized, the surgeon can select to trial off the rasp and thus remove the handle and adapter to allow for the trunnion trials to be installed. At this point the surgeon can disconnect the rasp handle with the rasp/adapter remaining in the canal of the bone (e.g., a femoral canal). The removal of the rasp handle can alleviate the lock allowing the surgeon to manually remove the adapter from the rasp. After successful trialing, the surgeon can replace the adapter and then the rasp handle to remove the rasp from the prepared bone.

Turning now to the figures, FIG. 1 illustrates proximal portions of rasps 100 and 150 in accordance with at least one example of the present disclosure. As shown in FIG. 1, rasp 100 can include a body 102 and a trunnion 104. Trunnion 104 can extend from a superior surface 106 and define a notch 108. Rasp 150 can include a body 152 and a trunnion 154. Trunnion 154 can extend from a superior surface 156 and define a notch 158.

Each of rasps 100 and 150 can be from the same manufacturer or different manufacturers. For example, rasp 100 can be a rasp manufactured by a first manufacturer and rasp 150 can be a rasp manufactured by a second manufacturer. Rasps 100 and 150 can also be manufactured by the same manufacturer but be different generations or designs for rasps.

Because rasps 100 and 150 are manufactured by two different manufacturers or are different generations and/or designs, the geometry for connecting rasps 100 and 150 to a handle can be different. For example, as shown in FIG. 1, the height of trunnions 104 and 154 may have a height difference represented by ΔH. Notches 108 and 158 can be different as well. For instance, notch 108 can have a "V" shape that includes two straight portions 110 and a curved bottom 112. Notch 158 can have a curved structure 160 of a constant radius, R. The differences in trunnion height and notch structure can prevent rasps 100 and 150 from being attachable to a single handle.

Figure 2:
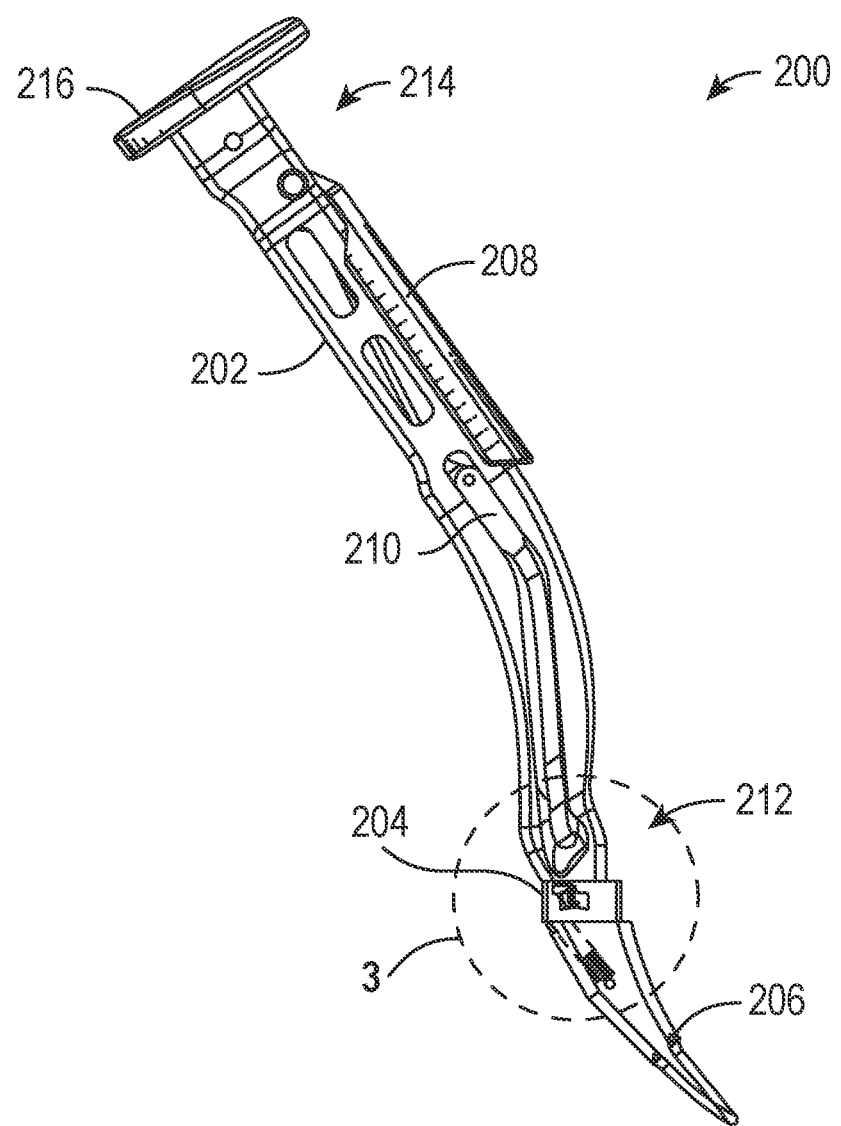
FIG. 2 shows a rasp system in accordance with at least one example of the present disclosure.

FIG. 2 shows a rasp system 200 in accordance with at least one example of the present disclosure. Rasp system 200 can include a handle 202, an adapter 204, and a rasp 206.

Rasp 206 can have a connection geometry similar to that of rasp 100 or rasp 150. As disclosed herein, rasp 206 has a connection geometry similar to that of rasp 150. Handle 202 can include a lever 208 that connects to a linkage 210. As shown in FIG. 2, handle 202 can include a first end 212 and a second end 214. Adapter 204 can be connected to first end 212 and an impaction head 216 can be connected to second end 214. Impaction head 216 can be removable to allow for customization of handle 202 and for replacement due to wear and tear over time.

Figure 3:
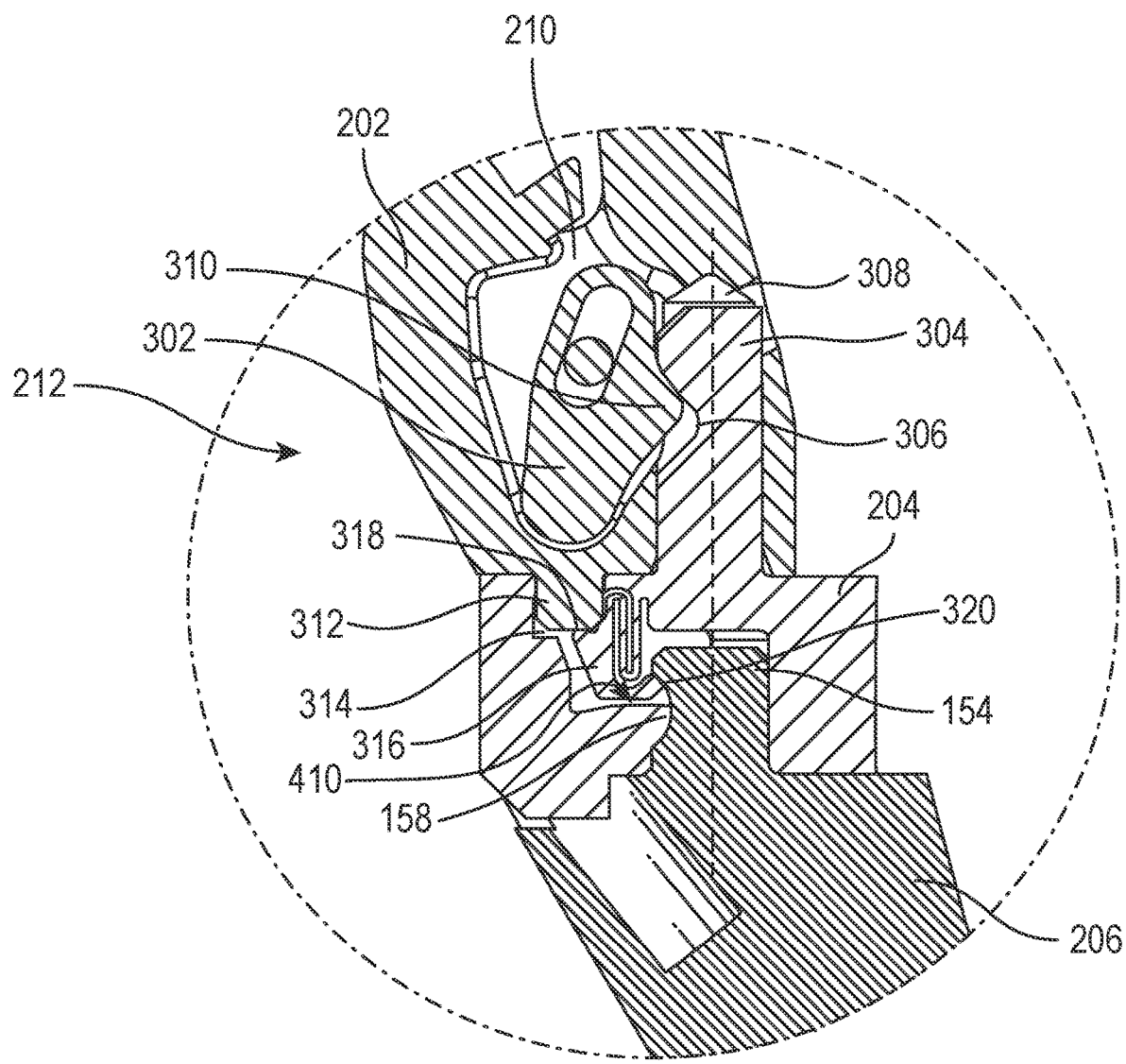
FIG. 3 shows a detail of the rasp system shown in FIG. 2 in accordance with at least one example of the present disclosure.

FIG. 3 shows a detail of adapter 204 and rasp 206 connected to handle 202. As disclosed herein, movement of lever 208 can cause movement of linkage 210 and a lock 302 so as to secure and release adapter 204 and rasp 206 to and from handle 202. As shown in FIG. 3, adapter 204 can include a trunnion 304 that defines a trunnion notch 306 and is located within a trunnion bore 308. In a locked state, a projection 310 of lock 302 can rest at least partially in trunnion notch 306 to secure adapter 204 to handle 202.

Handle 202 can include a pin 312 that extends from first end 212. Upon pin 312 entering adapter 204, via a handling opening 314, pin 312 can contact a retention element 316. For example, pin 312 can contact a heal 318 thereby causing a knuckle 320 to contact notch 158 thereby securing both adapter 204 and rasp 206 to handle 202.

Figure 4A:
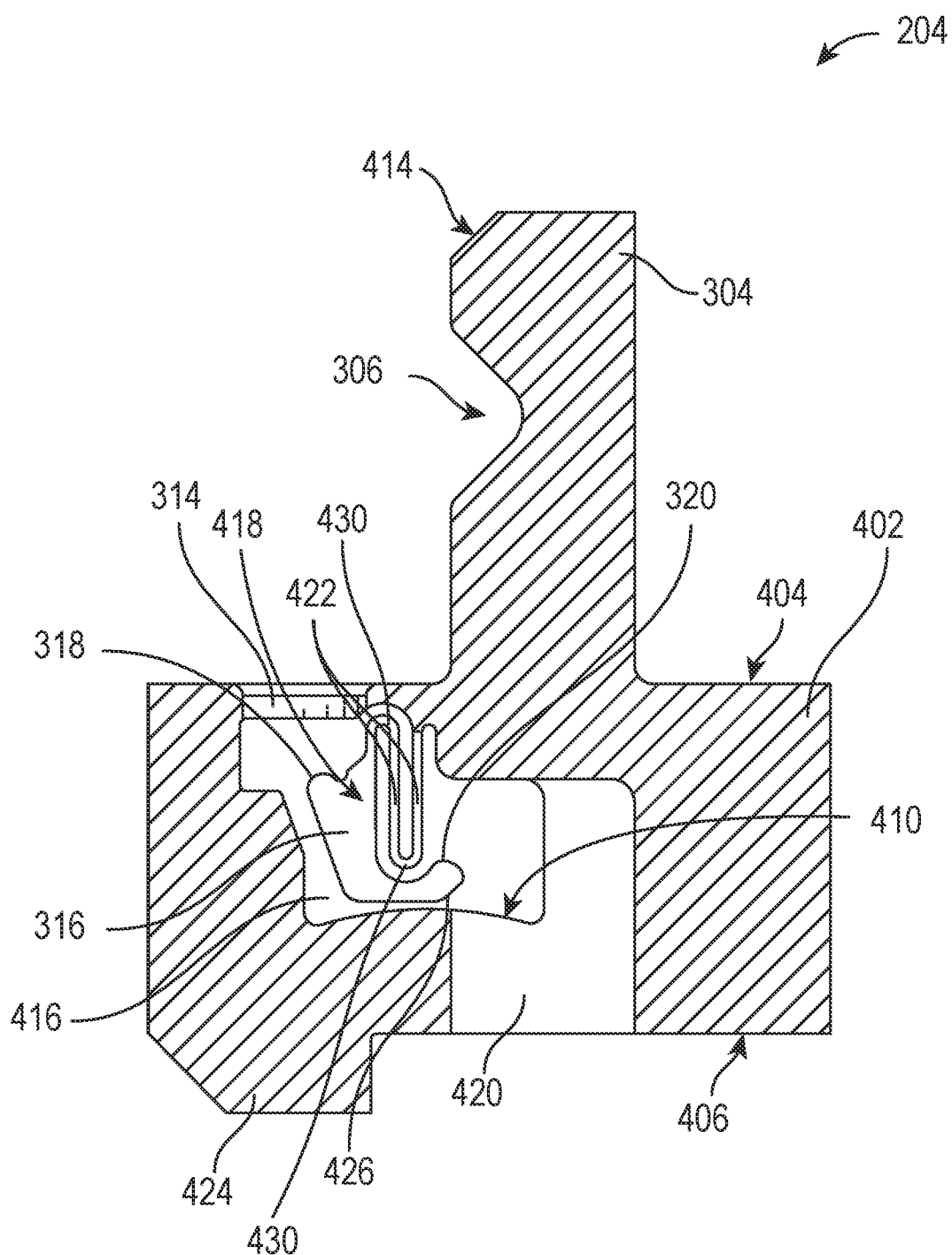
FIGS. 4A, 4B, 4C, and 4D each shows a rasp adapter in accordance with at least one example of the present disclosure.
Figure 4B:
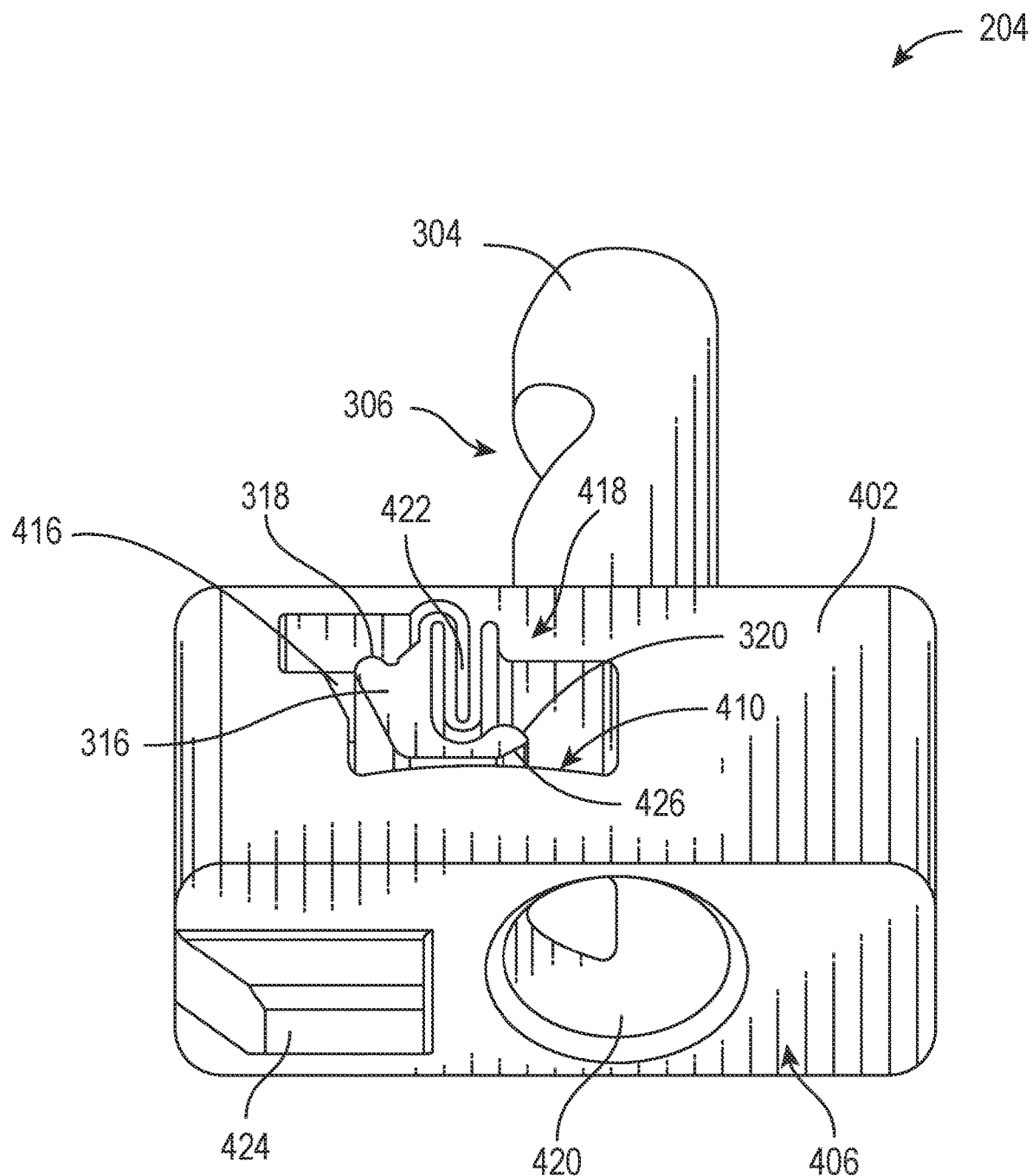
Figure 4C:
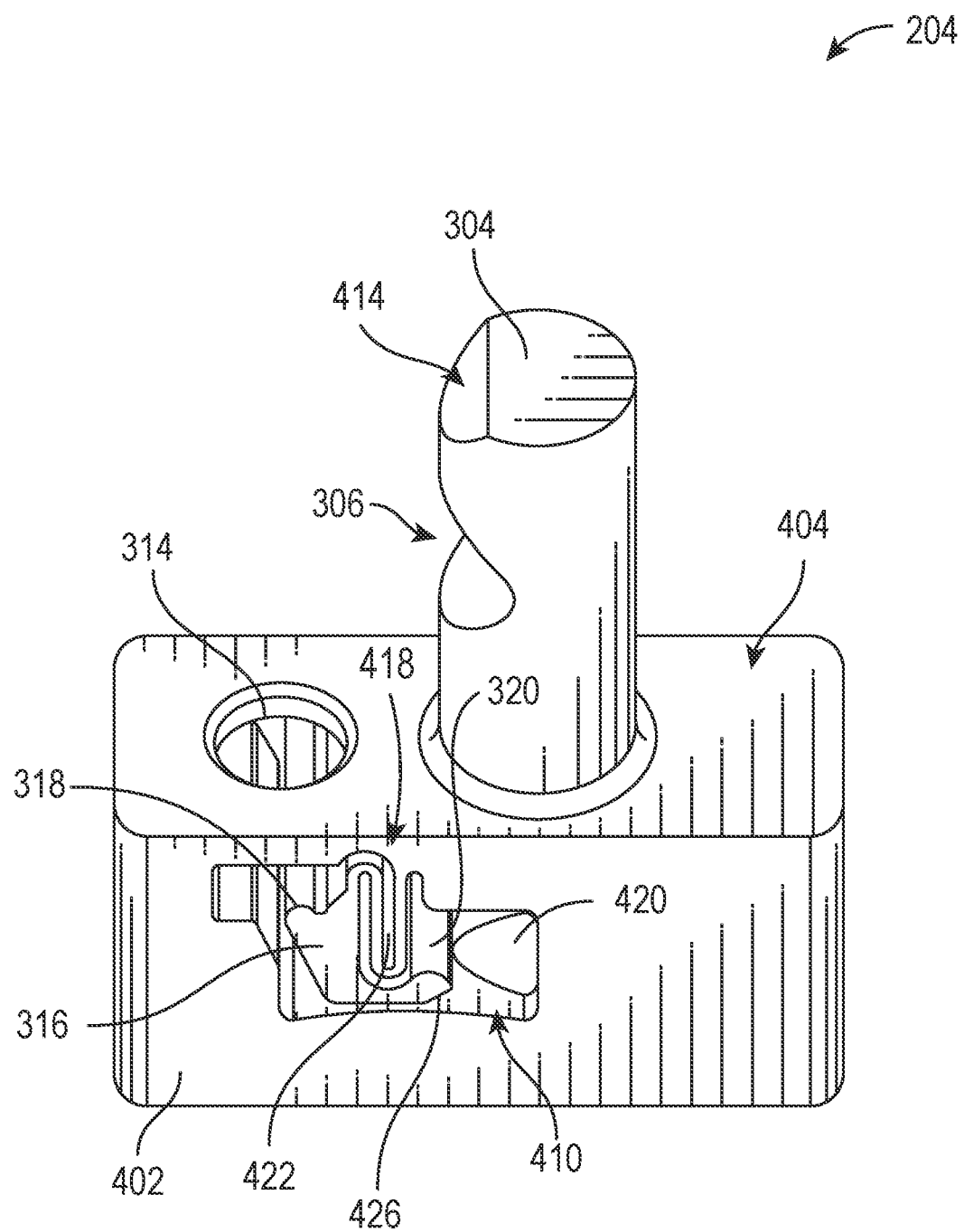

FIGS. 4A, 4B, and 4C shows adapter 204 in accordance with at least one example of the present disclosure. Adapter 204 can include a body 402 that can include a superior surface 404, an inferior surface 406, and an interior surface 410. Trunnion 304 can extend from superior surface 404. The trunnion 304 can define one or more trunnion notches 306. For example, trunnion 304 can have a length that allows for two trunnion notches to be formed thereby allowing adapter 204 to accommodate handles that have locks, such as lock 302, positioned different distances from a first end of a handle, such as first end 212 of handle 202. Trunnion 304 can also include a beveled surface 414. Beveled surface 414 can provide a transition to ease inserting adapter 204 into handle 202. For example, beveled surface 414 can contact lock 302 in order to cause lock 302 to move out of trunnion bore 308 when adapter 204 is inserted into handle 202.

The diameter of trunnion 304 can be constant and/or can vary. For example, the diameter of trunnion 304 can be constant as shows in FIGS. 4A-4C. the diameter of trunnion 304 can also vary as a function of distance from superior surface 404. For instance, trunnion 304 can have a slight conical shape.

Trunnion 304 and body 402 can be a monolithic component. For example, adapter 204 can be machined from a solid billet of metal such that trunnion 304 and body 402 are one continuous piece of metal. Still consistent with embodiments disclosed herein, trunnion 304 can be a threaded component that screws into body 402. For example, trunnion 304 can be machined from round stock with a threaded end and body 402 can include a tapped hole to allow trunnion 304 to be threaded into body 402.

Superior surface 404 can define handle opening 314. The size and shape of handle opening 314 can vary from one adapter to another. For example, adapter 204 can be one of a plurality of adapters that are part of a rasp system. Each of the adapters can have handle openings that vary depending on the handle in which they are designed to accommodate. As shown in FIGS. 4A and 4C, handle opening 314 can be circular. Still consistent with embodiments disclosed herein, handle opening 314 can be rectangular, oval shaped, pentagonal shaped, etc. Handle opening 314 can define a passage from the exterior of adapter 204 to a cavity 416 defined by interior surface 410. The passage can allow pin 312 to pass into cavity 416 and contact heal 318 of retention element 316.

As disclosed herein, retention element 316 can include heal 318 and knuckle 320. Retention element 316 can be secured to body 402 via a biasing element 418. Biasing element 418 can bias knuckle 320 into trunnion bore 420 defined by body 402. By having biasing element 418 biased into trunnion bore 420, when the trunnion of a rasp, such as trunnion 154 of rasp 206, is inserted into trunnion bore 420, knuckle 320 can move into a notch, such as notch 158 in trunnion 154, to temporarily secure the rasp to adapter 204. The biasing force applied by biasing element 418 can be high enough to secure rasp 202 to adapter 204 during general handling by surgeons or other operating room personnel but not so high as to require any special tools or other instruments to secure and/or remove trunnion 154 from adapter 204.

Biasing element 418 can be comprised of multiple elements. For example, as shown in FIGS. 4A-4C, biasing element 418 can be comprised of a plurality of spring legs 422 that can be connected together via curved portions 430. Other examples of biasing element 418 can include springs, such as torsional or compression springs.

Interior surface 410 can include an arched portion proximate retention element 318. The arched portion of interior surface 410 can have an apex that is located proximate retention element 318. As described below with respect to FIGS. 5A-5E, the arched portion of interior surface 410 can act as a stop to limit motion of retention element 318. In addition to or an in alternative to the arched portion of interior surface 410, a tab or other protuberance can extend from interior surface 410 to limit movement of retention element 318 when handle 202 is connected to adapter 204.

Adapter 204 can include a protrusion 424 that extends from inferior surface 406. As disclosed herein, protrusion 424 can mate with a complementary recess in rasp 206. While adapter 204 is shown and described as having protrusion 424 and rasp 206 as having the complementary recess, adapter 204 can have a complementary recess and rasp 206 can have a protrusion without departing from contemplated embodiments. Protrusion 424 can act to prevent rotation of rasp 206 in adapter 204.

As disclosed herein retention element 316 can include heal 318 and knuckle 320. Knuckle 320 can include a lead in 426. Lead in 426 can be a beveled portion or other angled surface of knuckle 320. Lead in 426 can allow a trunnion of a rasp, such as trunnion 154 of rasp 206 to move retention element 316 due to contact between the two elements, thereby temporarily moving retention element 316 out of trunnion bore 420. Upon a notch, such as notch 158, passing knuckle 320, knuckle 320 can move back into trunnion bore 420 and contact notch 158, thereby temporarily securing rasp 206 to adapter 204. The surface of knuckle 320 that contact notch 158 can be contoured to match notch 158. For example, notch 158 has a curved shape so the surface of knuckle 320 that contacts notch 158 can be curved as well. Notch 108 (see FIG. 1) has planar surface 110 so the surface of knuckle 320 that contacts notch 108 can be planar as well.

Adapter 204 can be manufactured from metals, polymers, ceramics, or any combination thereof. Adapter 204 can be manufactured via a variety of manufacturing techniques including, but not limited to, machining (CNC or manual), injection molded, overmolding, etc. For example, adapter 204 can be machined from a single metal billet (i.e. be a monolithic component). Adapter 204 can also be machined from a metal billet and overmolded with a rubber or other polymer. Various surfaces of adapter 204 can be overmolded or otherwise coated as well. For example, superior surface 404 and/or inferior surface 406 can be coated with a polymer or ceramic to help minimize wear between superior surface 404 and/or inferior surface 406 and surfaces of handle 202 and rasp 206.

Figure 4D:
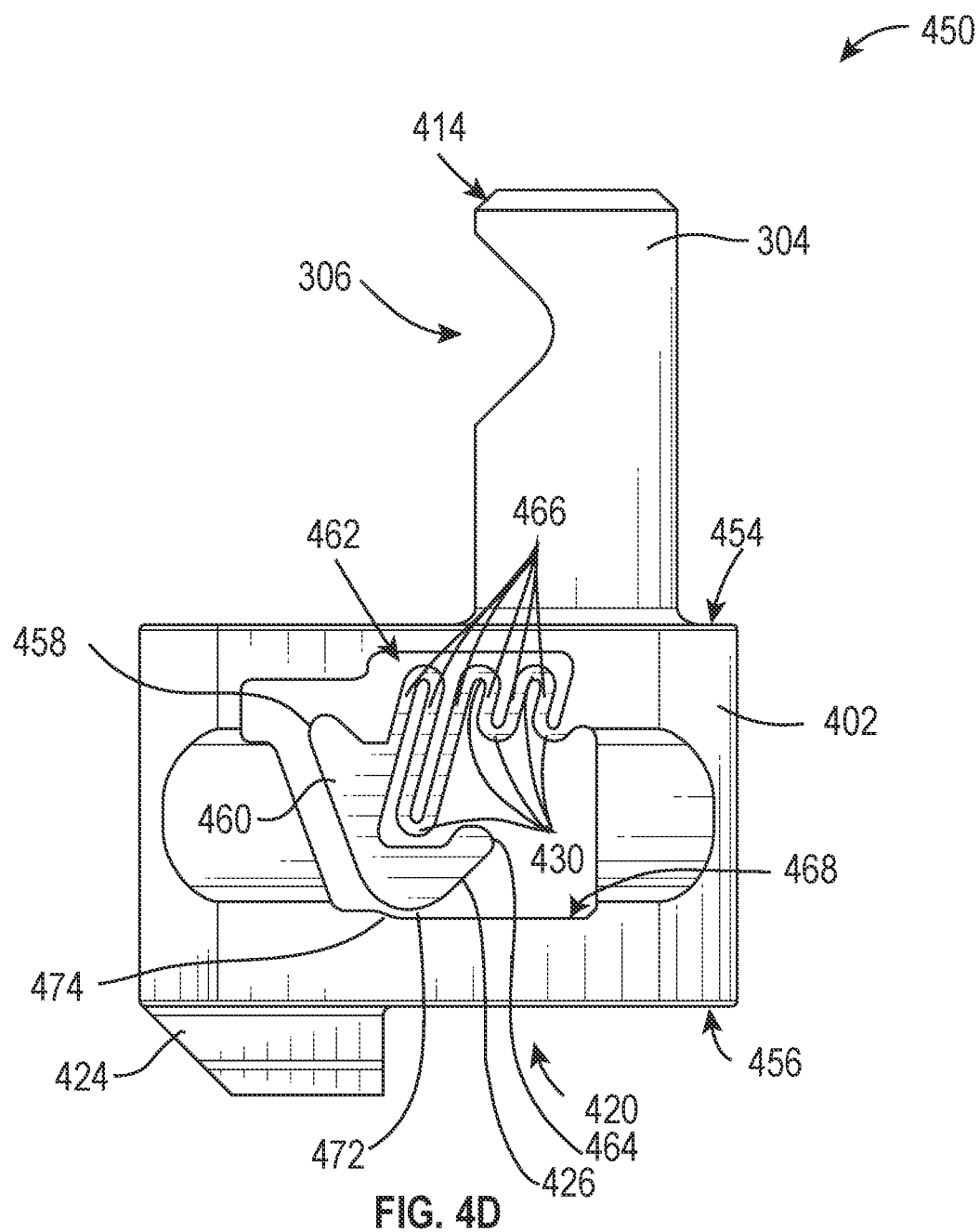

FIG. 4D shows adapter 450 in accordance with at least one example of the present disclosure. Adapter 450 can include a body 452 that can include a superior surface 454, an inferior surface 456, and an interior surface 458. Trunnion 304 can extend from superior surface 454. Trunnion 304 can define one or more trunnion notches 306 and a beveled surface 414 as disclosed with respect to FIGS. 4A-4C.

Adapter 450 can include a retention element 470 that can include a heal 458 and knuckle 460. Retention element 460 can be secured to body 402 via a biasing element 462. Biasing element 462 can bias knuckle 464 into trunnion bore 420 defined by body 402. By having biasing element 462 biased into trunnion bore 420, when the trunnion of a rasp, such as trunnion 154 of rasp 206, is inserted into trunnion bore 420, knuckle 464 can move into a notch, such as notch 158 in trunnion 154, to temporarily secure the rasp to adapter 204 as disclosed herein.

Biasing element 462 can be comprised of multiple elements. For example, as shown in FIG. 4D, biasing element 462 can be comprised of a plurality of spring legs 466 connected by arched portions 430. Other examples of biasing element 462 can include springs, such as torsional or compression springs. Spring legs 466 can be angled relative to the axis of trunnion bore 420 to provide additional clearance. In addition and as shown in FIG. 4D, individual legs of spring legs 464 can have different lengths relative to one another.

Interior surface 468 can be flat and retention element 460 can include an arched portion 472 proximate interior surface 468. Arched portion 472 can have an apex that is located proximate interior surface 468. As described herein, arched portion 472 and of interior surface 468 can act as a stop to limit motion of retention element 460. Interior surface 468 can also define a radius 474 that can act as a stop to limit motion of retention element 460 via contact with radius 474.

In addition to or an in alternative to arched portion 472, a tab or other protuberance can extend from retention element 460 or interior surface 468 to limit movement of retention element 460 when handle 202 is connected to adapter 204.

Adapter 450 can be manufactured from metals, polymers, ceramics, or any combination thereof. Adapter 450 can be manufactured via a variety of manufacturing techniques including, but not limited to, machining (CNC or manual), injection molded, overmolding, etc. For example, adapter 450 can be machined from a single metal billet (i.e. be a monolithic component). Adapter 450 can also be machined from a metal billet and overmolded with a rubber or other polymer. Various surfaces of adapter 450 can be overmolded or otherwise coated as well. For example, superior surface 454 and/or inferior surface 456 can be coated with a polymer or ceramic to help minimize wear between superior surface 454 and/or inferior surface 456 and surfaces of handle 202 and rasp 206.

Figure 5A:
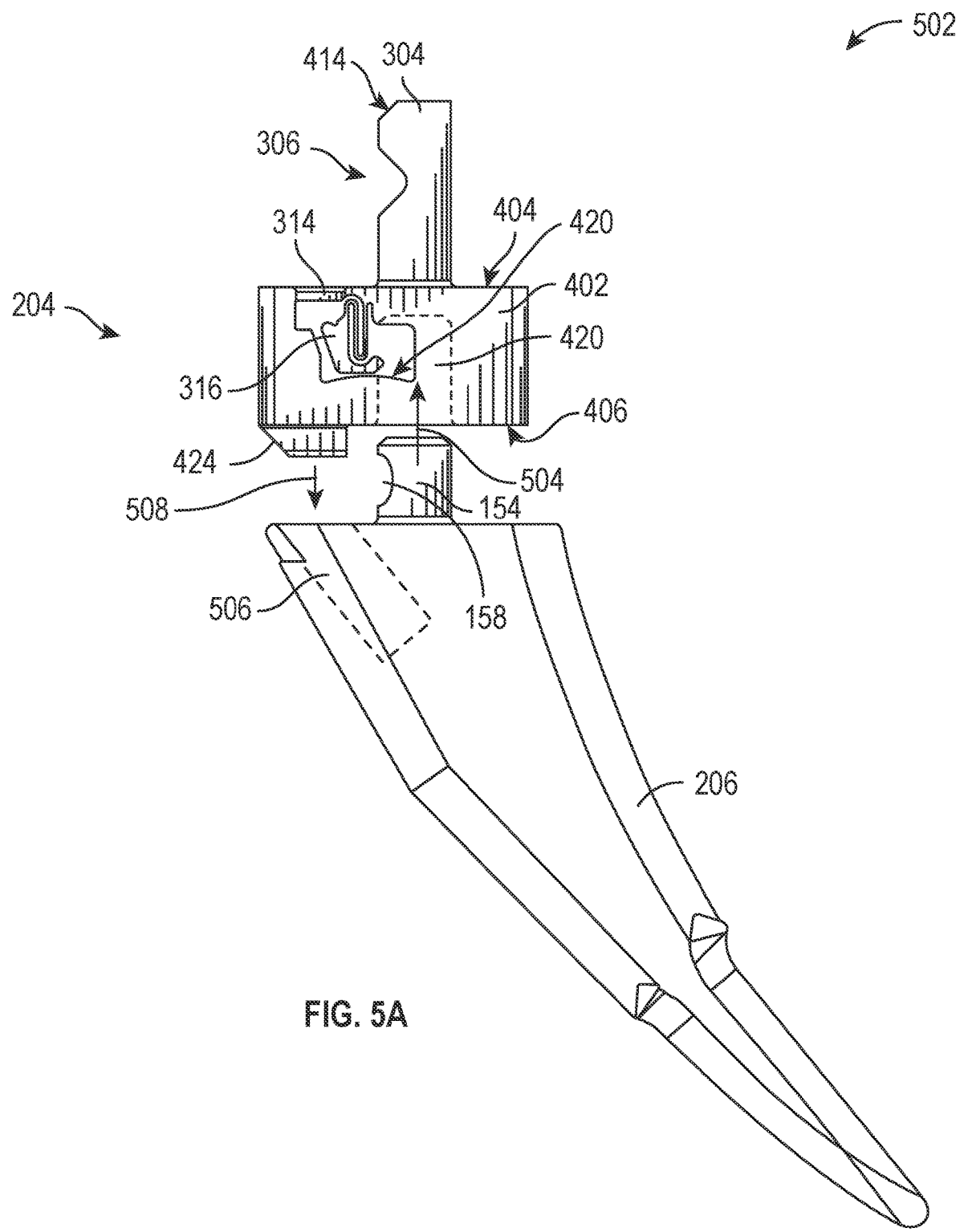
FIGS. 5A, 5B, 5C, 5D, and 5E show a method for assembling a rasp system in accordance with at least one example of the present disclosure.
Figure 5B:
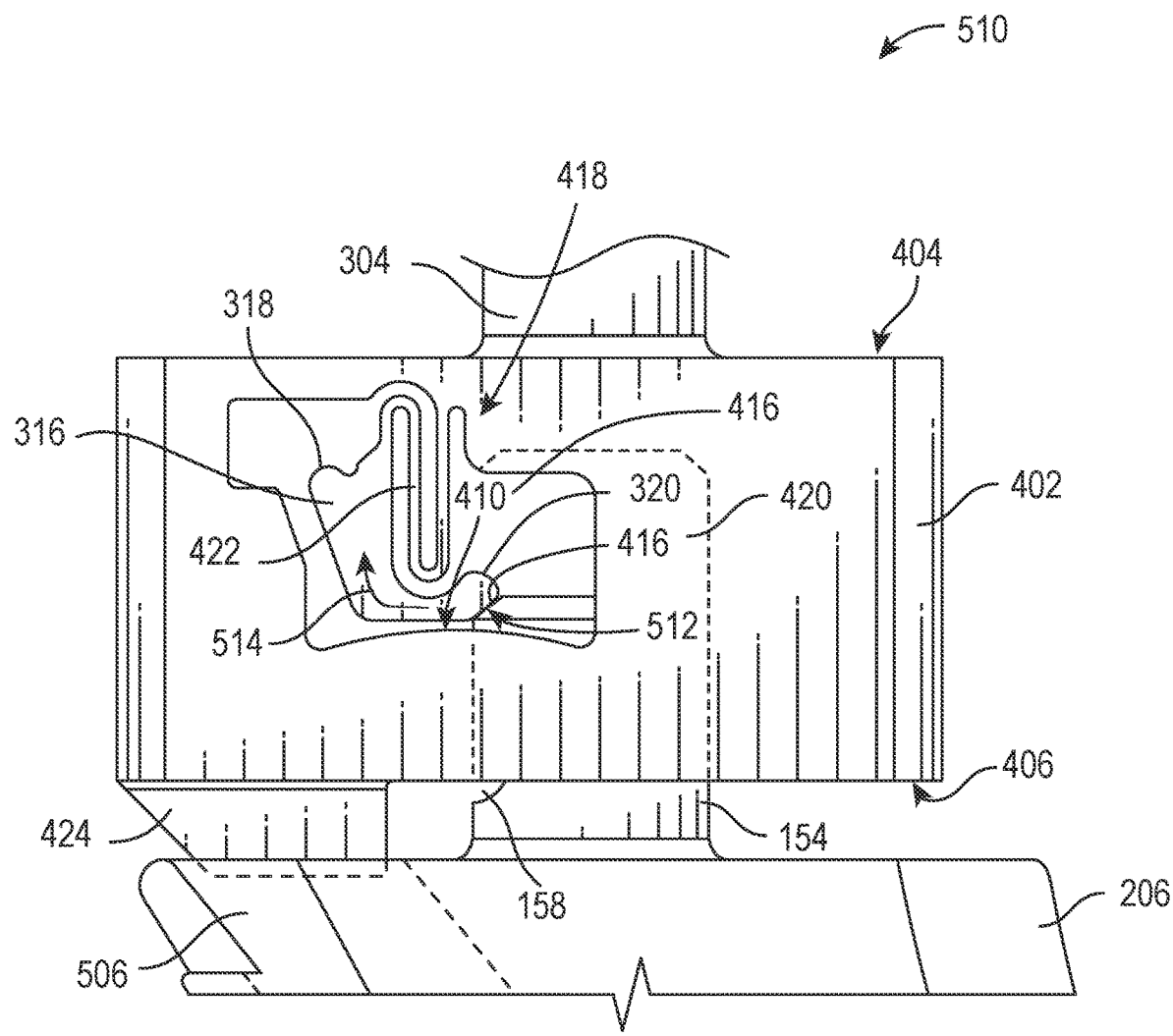
Figure 5C:
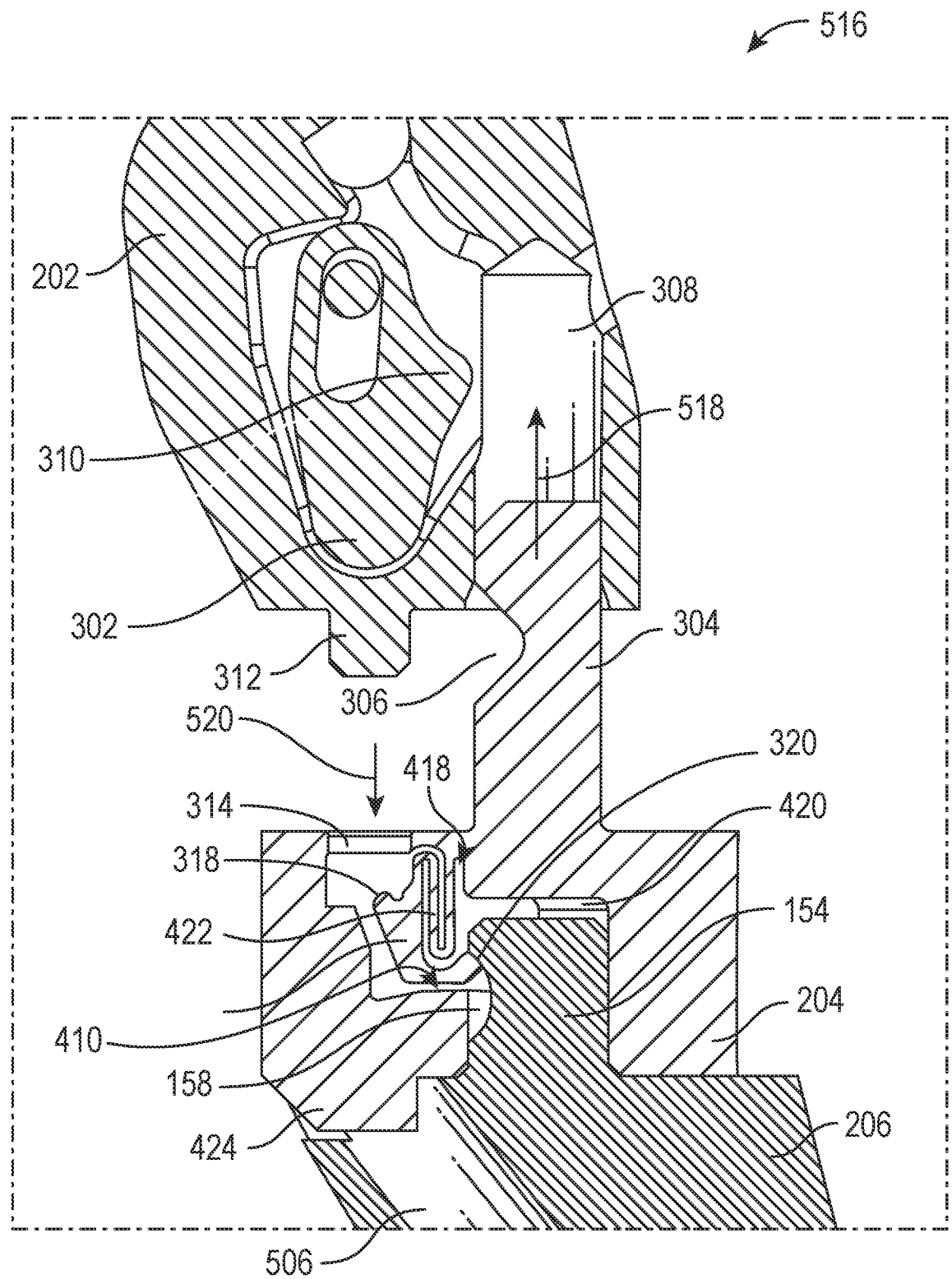

FIGS. 5A, 5B, 5C, 5D, and 5E show method stages for assembling rasp system 200 in accordance with at least one example of the present disclosure. The method can begin at stage 502 (FIG. 5A) where rasp 206 can be connected to adapter 204. To connect rasp 206 to adapter 204 trunnion 154 can be inserted into trunnion bore 420 as indicated by arrow 504 and pin 424 can be inserted into a recess 506 located in rasp 206 as indicated by arrow 508. As shown in FIG. 5B (stage 510), upon trunnion 154 entering cavity 416 a beveled surface 512 of trunnion 154 can contact lead in 416. Upon contacting lead in 416 trunnion 154 can cause movement, such as rotation and/or translation, as indicated by arrow 514, of retention element 316 so that knuckle 320 moves out of trunnion bore 420. Upon notch 158 passing knuckle 320, knuckle 320 can seat into notch 158 as shown in FIGS. 3 and 5C.

Figure 5D:
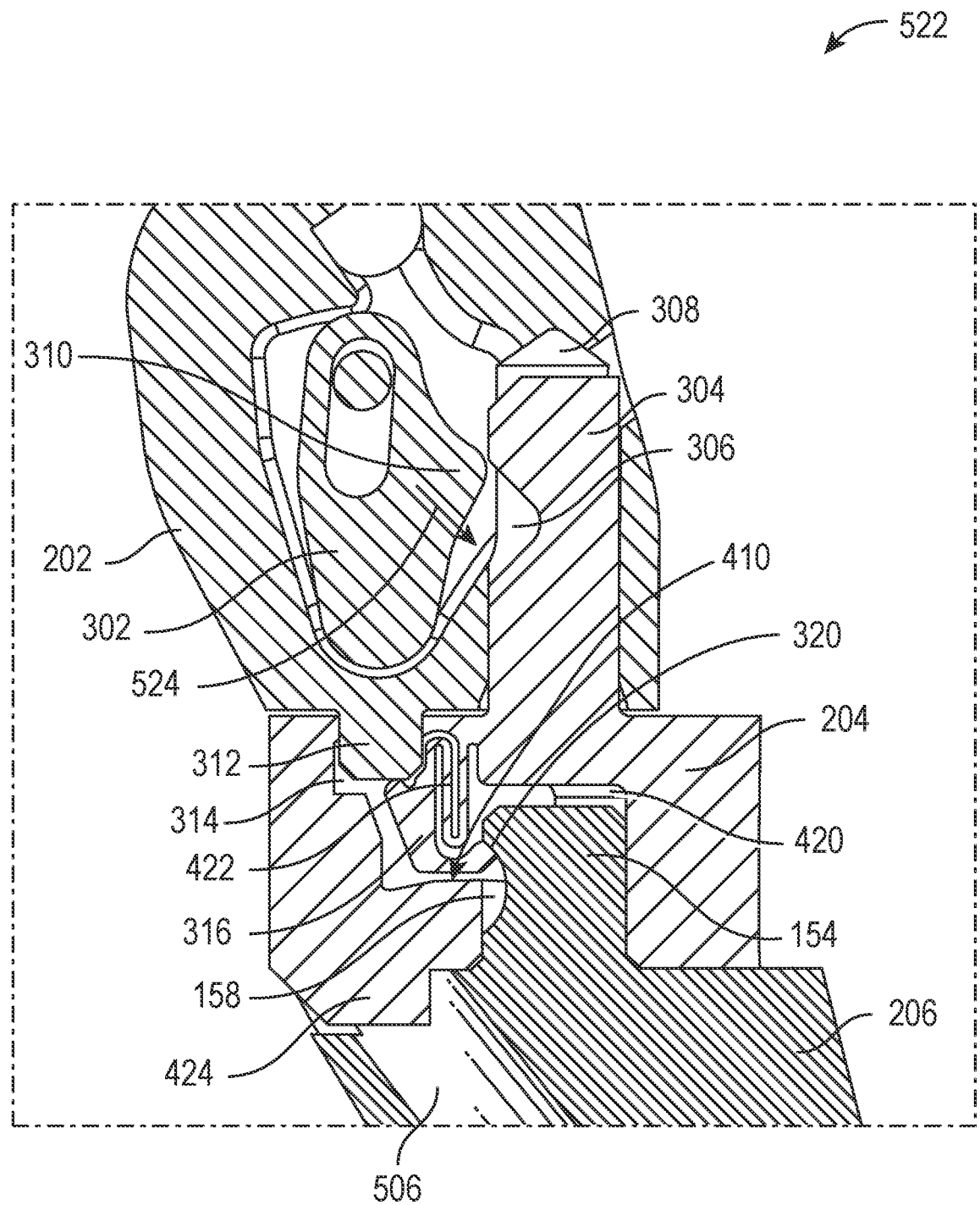

At stage 516 (FIG. 5C) trunnion 304 can be inserted into trunnion bore 308 as indicated by arrow 518. As trunnion 304 passes through trunnion bore 308, pin 312 can enter handle opening 314 as indicated by arrow 520. During stage 516, biasing element 422 can bias retention element 316 so that knuckle 320 holds rasp 206 in place. As trunnion 304 passes through trunnion bore 308, trunnion notch 306 can pass projection 310 as shown in FIG. 5D.

At stage 522 (FIG. 5D.) pin 312 can seat into handling opening 314 and protrusion 310 can be moved into trunnion notch 306. Movement of protrusion 310 and lock 302 can be caused by movement of level 208.

Figure 5E:
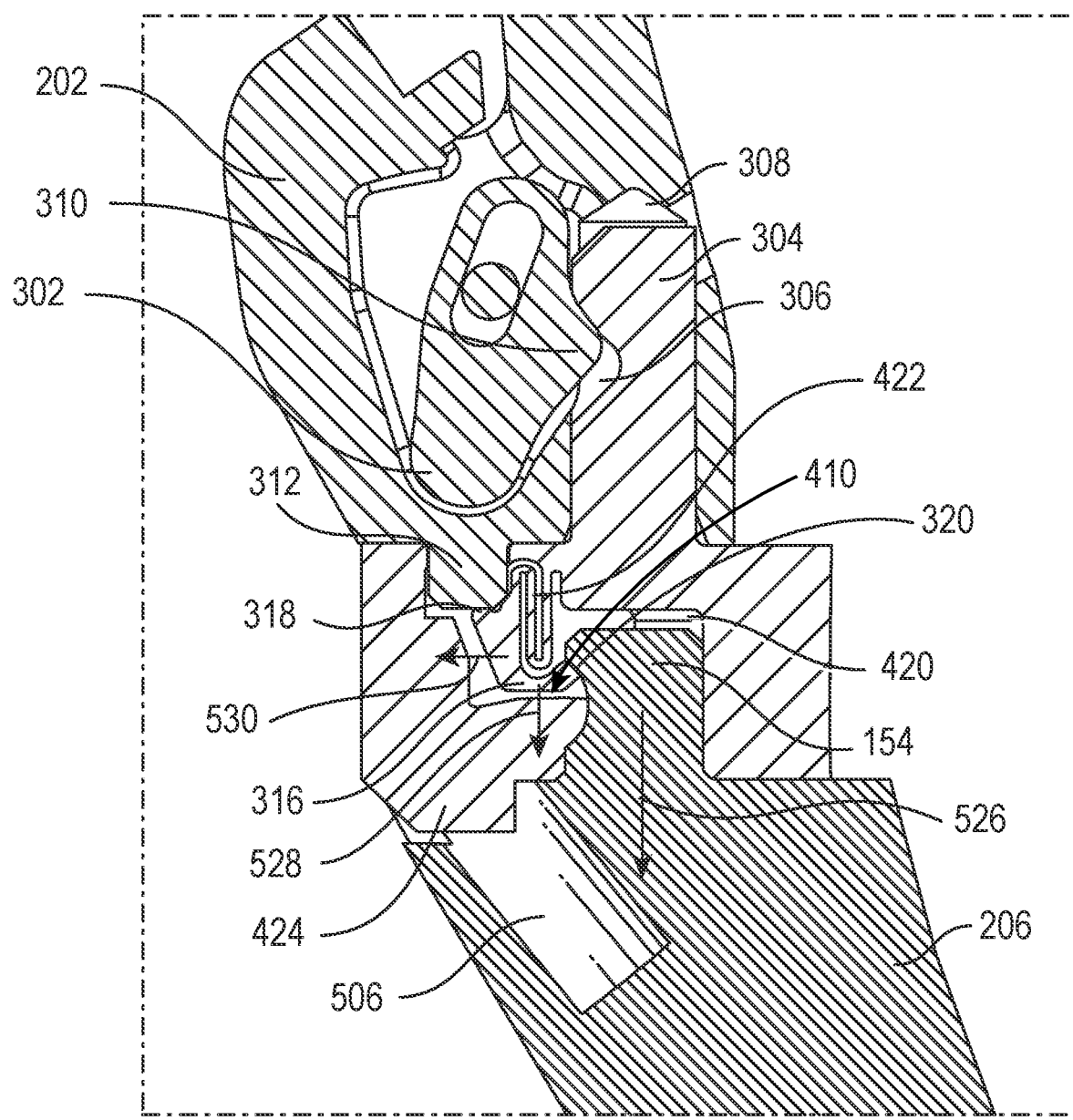

FIG. 5E shows rasp 206 secured to adapter 204, which is in turn secured to handle 202. As shown in FIG. 5E, pin 312 resting against heal 314 can act to constrict movement of retention element 316. In addition, the apex of interior surface 410 also can act to constrict movement of retention element 316. As shown in FIG. 5E, a downward force (indicated by arrow 526) can cause retention element 316 to move as indicated by arrow 528 and contact the curved portion or the apex of interior surface 410. The contact between knuckle 320 and interior surface 410 along with contact of pin 312 and heal 314 locks rasp 206 to adapter 204. Stated another way, by constricting movement of retention element 316 with interior surface 410 and pin 312, knuckle 320 forms a wedge that secures rasp 206 to adapter 204.

To remove rasp 206 from adapter 204, handle 202 can be removed so that pin 312 no longer restricts movement of retention element 316. For example, handle 202 can be removed from adapter 204. Once handle 202 is removed, retention element 316 is free to move as indicated by arrow 530 and rasp 202 can be pulled from adapter 204. For instance, as rasp 202 is pulled from adapter, the surface of knuckle 320 that contacts notch 158 can slide along notch 158 thereby pushing retention element out of trunnion bore 420 as indicated by arrow 530.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rasp adapter comprising:
   a body that defines a body cavity, a handle opening, and a trunnion bore; and
   a retention element located within the body cavity, the retention element including:
      a knuckle located proximate to and movable into and out of the trunnion bore, and
      a heal located proximate the handle opening,
   wherein movement of the retention element due to a force applied to the heal causes movement of the retention element and movement of the knuckle into the trunnion bore.

2. The rasp adapter of claim 1, wherein the retention element is coupled to the body via a spring.

3. The rasp adapter of claim 1, further comprising a trunnion protruding from a superior surface of the body, the trunnion defining at least one trunnion notch.

4. The rasp adapter of claim 3, wherein the trunnion, the retention element, and the body are a monolithic component.

5. The rasp adapter of claim 1, further comprising a protrusion extending from an inferior surface of the body.

6. The rasp adapter of claim 1, further comprising a stop located proximate the knuckle.

7. The rasp adapter of claim 1, wherein a surface of the body cavity defines an arch structure with an apex proximate the knuckle.

8. The rasp adapter of claim 1, wherein the knuckle defines a lead in proximate the trunnion bore.

9. The rasp adapter of claim 1, further comprising a pin pivotably coupling the retention element to the body.

10. The rasp adapter of claim 1, further comprising a biasing element located within the body cavity and arranged to bias the knuckle into the trunnion bore.

11. A rasp adapter comprising:
    a body having an interior surface that defines a body cavity, a handle opening, and a trunnion bore;
    a trunnion protruding from a superior surface of the body;
    a biasing element located within the body cavity; and
    a retention element located within the body cavity and coupled to the body via the biasing element, the retention element including:
       a knuckle located proximate to and moveable into and out of the trunnion bore, and
       a heal located proximate the handle opening,
    wherein movement of the retention element due to a force applied to the heal causes movement of the retention element and movement of the knuckle into the trunnion bore.

12. The rasp adapter of claim 11, wherein the biasing element comprises a plurality of spring legs.

13. The rasp adapter of claim 11, wherein the trunnion defines at least one trunnion notch.

14. The rasp adapter of claim 11, further comprising a protrusion extending from an inferior surface of the body.

15. The rasp adapter of claim 11, wherein the interior surface of the body cavity defines an arch structure with an apex proximate the knuckle.

16. The rasp adapter of claim 11, wherein the knuckle defines a lead in proximate the trunnion bore.

17. The rasp adapter of claim 11, wherein the biasing element, the retention element, and the body are a monolithic component.

18. A rasp system comprising:
    a handle having a first end that defines a first trunnion bore and a handle pin; and
    a plurality of adapters, each of the plurality of adapters comprising:
       a body having an interior surface that defines a body cavity, a handle opening sized to receive the handle pin, and a second trunnion bore;
       a trunnion protruding from a superior surface of the body, the trunnion defining at least one trunnion notch;
       a biasing element located within the body cavity; and
       a retention element located within the body cavity and coupled to the body via the biasing element, the retention element including a knuckle located proximate to and moveable into and out of the second trunnion bore, and a heal located proximate the handle opening,
    wherein the biasing element of at least one of the plurality of adapters comprises a plurality of spring legs,
    wherein the knuckle of at least one of the plurality of adapters defines a lead in proximate the second trunnion bore,
    wherein upon insertion of the handle pin into the handle opening and the trunnion into the first trunnion bore, the handle pin contacts the heal and causes the knuckle to move into the second trunnion bore, wherein a combination of trunnion and second trunnion bore sizes differs for each of the plurality of adapters.

19. The rasp system of claim 18, wherein at least one of the plurality of adapters comprises a protrusion extending from an inferior surface of the body.

20. The rasp system of claim 18, wherein the interior surface of at least one of the plurality of adapters defines an arch structure with an apex proximate the knuckle.

* * * * *